(12) United States Patent
Hung et al.

(10) Patent No.: US 6,391,026 B1
(45) Date of Patent: May 21, 2002

(54) METHODS AND SYSTEMS FOR TREATING BREAST TISSUE

(75) Inventors: David Hung, Belmont; Chris Ken, San Mateo; Julian Nikolchev, Portola Valley; Susan Love, Pacific Palisades; Shawn O'Leary, San Jose, all of CA (US)

(73) Assignee: Pro Duct Health, Inc., Menlo Park, CA (US)

( * ) Notice: Subject to any disclaimer, the term of this patent is extended or adjusted under 35 U.S.C. 154(b) by 0 days.

(21) Appl. No.: 09/397,753

(22) Filed: Sep. 16, 1999

Related U.S. Application Data

(60) Provisional application No. 60/100,853, filed on Sep. 18, 1998.

(51) Int. Cl.[7] ............................................... A61B 18/18
(52) U.S. Cl. ............................... 606/41; 606/2; 606/13; 606/14; 606/20; 606/27; 606/32
(58) Field of Search ........................... 606/2, 13, 14–16, 606/20, 27, 32, 40, 41, 46; 607/96, 101, 154; 128/898

(56) References Cited

U.S. PATENT DOCUMENTS

| | | | |
|---|---|---|---|
| 4,556,057 A | * 12/1985 | Hiruma et al. | ................. 604/20 |
| 5,472,441 A | 12/1995 | Edwards et al. | |
| 5,540,737 A | 7/1996 | Fenn | |
| 5,763,415 A | 6/1998 | Sukumar | |
| 5,766,222 A | 6/1998 | Petit | |
| 5,803,913 A | 9/1998 | Khalkahi et al. | |
| 5,807,395 A | 9/1998 | Mulier et al. | |
| 6,163,726 A | * 12/2000 | Wolf | ........................ 607/101 |

FOREIGN PATENT DOCUMENTS

| WO | WO 97/05898 | 2/1997 |
|---|---|---|

OTHER PUBLICATIONS

Barsky et al., "Pathological analysis of breast duct endoscoped mastectomies" Laboratory Investigation, Modern Pathology (1996)Abstract 67, p. 15A.

Fabian et al. "Prevalence of abnormal biomarkers in fine needle breast aspirates in a high risk population: Potential for use in risk prediction" Proc. Ann. Meet. Am. Assoc. Cancer Res. (1993) 34:A1556.

Imayama et al. "Presence of elevated carcinoembryonic antigen on absorbent disks applied to nipple area of breast carcinoma patients" Cancer (1996) 78(6):1229–1234.

Lewis et al. "Technique probes breast ducts for cancer cells" Biophotonics International (1997) pp. 27–28.

Love et al., "Breast–duct endoscopy to study stages of cancerous breast disease" Lancet (1996) 348:997–999.

Love et al., "Breast duct endoscopy: A pilot study of a potential technique for evaluating intraductal disease" 15th Annual San Antonio Breast cancer Symposium, San Antonio, TX (1992) Abstract 197 (1 page total).

Makita et al., "Duct endoscopy and endoscopic biopsy in the evaluation of nipple discharge" Breast Cancer research and Treatment (1991) 18:179–188.

Okazaki et al., "Fiberoptic ductoscopy of the breast: A new diagnostic procedure for nipple discharge" Jpn. J. Clin. Oncol. (1991) 21(3):188–193.

(List continued on next page.)

Primary Examiner—R. Kearney
(74) Attorney, Agent, or Firm—Banner & Witcoff, Ltd.

(57) ABSTRACT

Methods, systems, and kits for treating breast tissue rely on transferring energy to or from cells lining an individual breast duct. Energy can be introduced into the breast duct, e.g., by filling the duct with an electrically conductive medium and applying radiofrequency energy to the medium. Other energy forms could also be used, such as light, ultrasound, radiation, microwave energy, heat, cold, direct current, and the like. By treating individual breast ducts, cancerous and pre-cancerous conditions originating in the duct can be effectively treated.

55 Claims, 12 Drawing Sheets

OTHER PUBLICATIONS

Petrakis et al. "Studies on the epidemiology and natural history of benign breast disease and breast cancer using nipple aspirate fluid" Cancer Epidem. Biomarker Prev. (1993) 2:3–10.

Petrakis et al. "Nipple aspirate fluid in epidemiologic studies of breast disease" Epidem. Rev. (1993) 15:188–195.

Petrakis et al. "Physiologic, biochemical, and cytologic aspects of nipple aspirate fluid" Breast Cancer and Treatment (1986) 8:7–19.

Sartorius et al. "The biochemistry of breast cyst fluids and duct secretions" Breast Cancer and Treament (1995) 35:255–266.

Sartorius et al., "Contrast ductography for recognition and localization of benign and malignant breast lesions: An improved technique" Breast Carcinoma, Logan (ed.) New York, Wiley & Sons Publishers 91977) pp. 281–300.

Wrensch et al., "Breast cancer incidence in women with abnormal cytology in nipple aspirates of breast fluid" Am. J. Epidem. (1992) 135(2):130–141.

Wrensch et al., "Factors associated with obtaining nipple aspirate fluid: Analysis of 1428 women and literature review" Breast Cancer and Treatment (1990) 15:39–51.

Wrensch et al., "Breast fluid cholesterol and cholesterol β–epoxide concentrations in women with benign breast disease" Cancer Research (1989) 49:2168–2174.

Baum et al., "Radioimmunolocalization of primary and metastatic breast cancer" Q. J. Nucl. Med. (1998) 42(1):333–42.

DeLand et al., "Axillary lymphoscintigraphy by radioimmunodetection of carcinoembryonic antigen in breast cancer" J. Nucl. Med. (1979) 20(12):1243-12–50.

Goldenberg, "Perspectives on oncologic imaging with radiolabeled antibodies" Cancer (1997) 80(12):2431–2435.

Goldenberg et al., "Breast cancer imaging with radiolabeled antibodies" Seminars in Nuclear Medicine (1999) XXIX(1):41–48.

Hoh et al., "18–FDG Imaging in breast cancer" Seminars in Nuclear Medicine (1999) XXIX(1):49–56.

Juweid et al., "Improved detection of medullary thyroid cancer with radiolabeled antibodies to carcinoembryonic antigen" J. Clin. Oncol. (1996) 14(4):1209–1217. Article abstract enclosed from http://www.ncbi.nlm.nih.gov.

Kairemo, "Immunolymphoscintigraphy with $^{99m}$Tc–labeled monoclonal antibody (BW 431/26) reacting with carcinoembryonic antigen in breast cancer" Cancer Research (1990) 50:949s–954s.

Kairemo et al., "Radioimmunoimaging of glomus typanicum tumors by In–111 labeled monoclonal antibody using single photon emission computed tomography" Am. J. Otol. (1997) 18:750–753.

Lamberts et al., "Somatostatin and the concept of peptide receptor scintigraphy in oncology" (1994) 21(5):1–5.

Lind et al., "The immunoscintigraphic use of Tc–99m–labeled monoclonal anti–cea antibodies (BW 431/26) in patients with suspected primary, recurrent and metastatic breast cancer" Int. J. Cancer (1991) 47:865–869.

Low et al., "Ovarian cancer: Comparison of findings with perfluorocarbon–enhanced MR imaging, In–111CYT–103 immunoscintigraphy, and CT" Radiology (1995) 195(2):391–400. Article abstract enclosed from http://www.ncbi.nlm.nih.gov.

Major et al., "Breast cancer imaging with mouse monoclonal antibodies" Eur. J. Nucl. Med. (1989) 15:655–660.

Major et al., "Breast tumor radioimmunodetection with a $^{111}$In–labeled monoclonal antibody (MA5) against a mucin–like antigen" Cancer Research (1990) 50:927s–931s.

Nabi, "Antibody imaging in breast cancer" Seminars in Nuclear Medicine (1997) XXVII(1):30–39.

Nakada et al., "Imaging of recurrent intestinal carcinoma with indium–111–labeled anti–carcinoembryonic antigen monoclonal antibody CEA102" Japanese J. Cancer Res. (1997) 88(6):605–613. Article abstract enclosed from http://www.ncbi.nlm.nih.gov.

Pansera, "Accessibility and possibility of elimination of breast epithleium: The theoretical possibility of preventing breast carcinoma through destruction of the epithelium of origin" Medical Hypothesis (1990) 33:107–111.

Robinson et al., "Interstitial laser hyperthermia model development for minimally invasive therapy of breast carcinoma" (1998) J. Am. Coll. Surg. 186:284–292.

Rosner et al., "Diagnosis of breast carcinoma with radiolabeled monoclonal antibodies (MoAbs) to carcinoembryonic antigen (CEA) and human milk fat globulin (HMFG)" Cancer Investigation (1995) 13(6):573–582.

Schatten et al., "Clinical value of immunolympscintigraphy in patients with breast cancer" In vivo (1988) 2:321–324.

Schatten et al., "Lymphoscintigraphy with $^{123}$I–labeled epidermal growth factor" Lancet (1991) 337:395–396.

Schatten et al., "Combined use of $^{123}$I–labeled BCD–F9 and 4C4 monoclonal antibody with dissimilar specificity for breast cancer: Implication for the detection limit of immunolymphoscintigraphy in the assessment of axillary lymph node metastases" Nulcear Med. Commun. (1994) 15:422–429.

Sipkins et al., "Detection of tumor angiogenesis in vivo by $α_vβ_3$–targeted magnetic resonance imaging" Nature Medicine (1998) 4(5):623–626.

Sodee et al., "Preliminary imaging results using In–111 labeled CYT–356 (prostascint) in the detection of recurrent prostate cancer" Clin. Nucl.Med. (1996) 21(10):756–767. Article abstract enclosed from http://www.ncbi.nlm.nih.gov.

Taillefer, "The role of 99mTc–sestamibi and other conventional radiopharmaceuticals in breast cancer diagnosis" Seminars in Nuclear Medicine (1999) XXIX(1):16–40.

Suwa et al., "Magnetic resonance imaging of esophageal squamous cell carcinoma using magnetite particles coated with anti–epidermal growth factor receptor antibody" Int. J. Cancer (1998) 75:626–634.

Tjandra et al., "Immunolymphoscintigraphy for the detection of lymph node metastases from breast cancer" Cancer Res. (1989) 49:1600–1608.

To et al., Monoclonal antibody–coated magnetite particles as contrast agents for MR imaging and laser therapy of human tumors J. Clin. Laser Med. Surg. (1992) 10(3):159–169. Article abstract enclosed from http://www.ncbi.nlm.nih.gov.

Vicini et al., "Implementation of 3D–virtual brachytherapy in the management of breast cancer: A description of a new method of interstitial brachytherapy" Int. J. Radiat. Oncol. Biol. Phys. (1998) 40(3):692–635. Article abstract enclosed from http://www.ncbi.nlm.nih.gov.

Profio et al. "Scientific basis of breast diaphanography." Med Phys 16(1), Jan./Feb. 1989.

Sartorius. "Fluid cytology and contrast ductography".

* cited by examiner

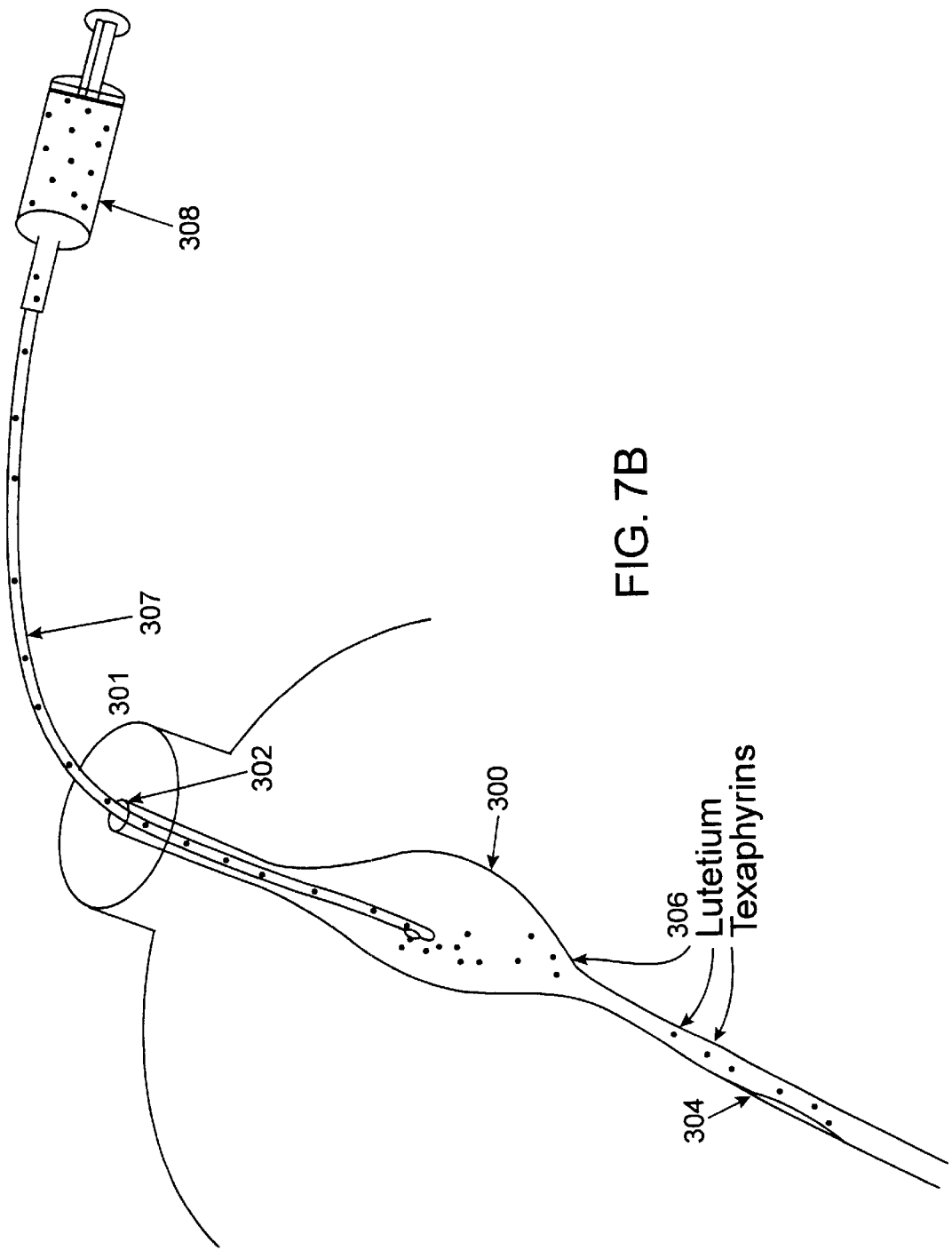

METHODS AND SYSTEMS FOR TREATING BREAST TISSUE

CROSS-REFERENCES TO RELATED APPLICATIONS

This application is a non-provisional filing which claims the benefit of provisional application No. 60/100,853, filed on Sep. 18, 1998 under 37 CFR 1.78(a). The full disclosure of application No. 60/100,853, is incorporated herein by reference.

BACKGROUND OF THE INVENTION

1. Field of the Invention

The present invention relates generally to medical methods and apparatus for treating breast tissues. More particularly, the present invention relates to methods and apparatus for ablating or inhibiting the proliferation of epithelial and other cells lining a breast duct.

Breast cancer is the most common cancer in women, with well over 100,000 new cases being diagnosed each year in the United States alone. Breast cancer usually begins in the cells lining a breast duct, with the first stage thought to be excessive proliferation of individual cell(s) leading to "ductal hyperplasia." Some of the hyperplastic cells may then become atypical, with a significant risk of the atypical hyperplastic cells becoming neoplastic or cancerous. Initially, the cancerous cells remain in the breast ducts, and the condition is referred to as ductal carcinoma in sitU (DCIS). After a time, however, the cancerous cells are able to invade outside of the ductal environment, presenting the risk of metastases, which can be fatal to the patient.

While breast cancer through the DCIS phase is in theory quite treatable, effective treatment requires both early diagnosis and an effective treatment modality. At present, mammography is the state-of-the-art diagnostic tool for detecting breast cancer. Often, however, mammography is only able to detect tumors, which have reached a size in the range from 0.1 cm to 1 cm. Such a tumor mass may be reached as long as from 8 to 10 years following initiation of the disease process. Detection of breast cancer at such a late stage is often too late to permit effective treatment.

Alternative diagnostic modalities, which promise much earlier detection of breast cancer and DCIS, are described in co-pending application Ser. Nos. 08/931,786; 09/067,661; and 09/301/058, the full disclosures of which are incorporated herein by reference. Together, these applications describe techniques for identifying one or more (usually all) individual ductal orifices on a nipple in a breast and for collecting cellular and other materials from individual ductal networks to determine if hyperplasia, DCIS, or other abnormal conditions are present in that network. While these techniques will be very useful in providing early and accurate diagnosis of breast cancer and other diseased conditions, they do not directly provide for treatment of the condition once it is diagnosed.

Conventional treatments for breast cancer have been focused on the treatment of a latter stage disease and include removal of the breast, localized removal of the tumor ("lumpectomy"), radiation, and chemotherapy. While these techniques are often very effective, they suffer from certain deficiencies. Removal of the breast provides the best assurance against recurrence of the cancer, but is disfiguring and requires the patient to make a very difficult choice. Lumpectomy is less disfiguring, but is associated with greater risk of recurrence of the cancer. Radiation and chemotherapy are arduous and are not completely effective against recurrence. Such conventional treatments will not always be able to take full advantage of emerging diagnostic techniques, which promise to allow detection of pre-cancerous and cancerous conditions in the breast at a very early stage.

For these reasons, it would be desirable to provide improved and alternative techniques for treating breast cancer and pre-cancerous conditions such as ductal carcinoma in situ (DCIS) and atypical ductal hyperplasia (ADH). In particular, it would be desirable to provide treatment modalities, which can be used in conjunction with the newly developed techniques for diagnosing DCIS and other abnormal conditions within individual breast ducts. Such techniques should be less invasive and traumatic to the patient than the present techniques, should result in minimum or no disfigurement of the breast, and should be effective locally within target sites within the breast duct and/or throughout an entire ductal network. Preferably, the techniques should be capable of being performed in a single or very few treatment session(s). At least some of these objectives will be met by the invention described hereinafter.

2. Description of the Background Art

Co-pending application Ser. Nos. 08/931,786; 09/067, 661; and 09/301,058 have been described above. Publications by the inventor herein relating to breast duct access include Love and Barsky (1996) *Lancet* 348: 997–999; Love (1992) "Breast duct endoscopy: a pilot study of a potential technique for evaluating intraductal disease," presented at 15th Annual San Antonio Breast Cancer Symposium, San Antonio, Tex., Abstract 197; Barsky and Love (1996) "Pathological analysis of breast duct endoscoped mastectomies," Laboratory Investigation, Modern Pathology, Abstract 67. A description of the inventor's earlier breast duct access work was presented in Lewis (1997) Biophotonics International, pages 27–28, May/June 1997.

Nipple aspiration and/or the introduction of contrast medium into breast ducts prior to imaging are described in Sartorius (1995) *Breast Cancer Res. Treat.* 35: 255–266; Satorius et al. (1977) "Contrast ductography for the recognition and localization of benign and malignant breast lesions: An improved technique," in: Logan (ed.), Breast Carcinoma, New York, Wiley, pp. 281–300; Petrakis (1993) *Cancer Epidem. Biomarker Prev.* 2: 3–10; Petrakis (1993) *Epidem. Rev.* 15: 188–195; Petrakis (1986) *Breast Cancer Res. Treat.* 8: 7–19; Wrensch et al. (1992) *Am. J. Epidem.* 135: 130–141; Wrensch et al. (1990) *Breast Cancer Res. Treat.* 15: 39–51; and Wrensch et al. (1989) *Cancer Res.* 49: 2168–2174. The presence of abnormal biomarkers in fine needle breast aspirates is described in Fabian et al. (1993) *Proc. Ann. Meet. Am. Assoc. Cancer Res.* 34: A1556. The use of a rigid 1.2 mm ductoscope to identify intraductal papillomas in women with nipple discharge is described in Makita et al. (1991) *Breast Cancer Res. Treat.* 18: 179–188. The use of a 0.4 mm flexible scope to investigate nipple discharge is described in Okazaki et al. (1991) *Jpn. J Clin. Oncol.* 21: 188–193. The detection of CEA in fluids obtained by a nipple blot is described in Imayama et al. (1996) *Cancer* 78: 1229–1234. Delivery of epithelium-destroying agents to breasts by ductal cannulation is described in WO 97/05898 and U.S. Pat. No. 5,763,415.

A company called Diagnostics Inc., formed in 1968, produced devices to obtain breast ductal fluid for cytological evaluation. The devices included a breast nipple aspiration device to collect NAF (nipple aspirate fluid) from subjects, and catheters to retrieve ductal fluid from breast ducts. The devices were sold prior to May 28, 1976 for the purpose of collecting breast ductal fluid for cytological evaluation.

Energy-mediated ablation of the uterus, gall bladder, blood vessels, and other hollow body organs are described in the following U.S. Pat. Nos.: 4,776,349; 4,869,248; 4,872,458; 4,979,948; 5,045,056; 5,100,388; 5,159,925; 5,222,938; 5,277,201; 5,242,390; 5,403,311; 5,433,708; 5,507,744; and 5,709,224.

SUMMARY OF THE INVENTION

The present invention provides improved methods for treating individual milk ducts in human and animal breasts. Such treatments will usually be performed in patients diagnosed with cancer or precancerous conditions but may also find use prophylactically in patients at risk of cancer or other ductal diseases. Treatment is directed at individual ducts in ductal networks within the breast and typically comprises transferring energy to or from a lumen of the duct in an amount sufficient to destroy (ablate) or inhibit proliferation of cells lining the duct, such as epithelial cells which are atypical, excessively proliferating (neoplastic), and/or at risk of excessive proliferation. In an exemplary embodiment, high frequency electrical current is directed to the lumen in order to ablate or necrose at least a portion of the cellular lining of the duct. The present invention also encompasses directing other forms of energy to the lumen of the duct, including light energy, vibrational energy (e.g., ultrasonic or sonographic), radiation (electromagnetic, ultraviolet, infrared, nuclear (typically $\beta$ but some times $\alpha$ and/or $\gamma$), x-ray, etc.), heat, direct electrical current, microwave, ferromagnetic, and the like. Cryogenic treatment may also find use with suitable cryogenic delivery systems as described, for example, in U.S. Pat. Nos. 5,899,898 and 5,147,355, the full disclosures of which are incorporated herein by reference. Photodynamic therapy employing light with wavelengths from ultraviolet to infrared may find use with known photoactive agents, such as porfimer sodium (PHOTOFRIN®), lutetium texaphrin (Antrin®), temoporfin (Foscan®), aminolevulinic acid HCl (Levula®), and the like. Exemplary phorphyrins and methods of making and other potential aids in the process of using them against breast cancer are described in U.S. Pat. Nos. 4,935,498, 5,159,065, 5,292,414, 5,369,101, 5,439,570, 5,451,576, 5,457,183, 5,530,122, 5,567,687, 5,587,371, 5,587,463, 5,607,924, 5,756,726, 5,776,925, 5,801,229, 5,817,017, and 5,837,866. Usually, the photoactive agent will be directed into an individual ductal network and light radiation directed to the ductal network and/or the entire breast. For example, the light may be introduced into the ductal network using a light fiber or waveguide in the form of a ductal access tool. Alternatively or additionally, light can be directed onto and through the exterior of the breast.

Other forms of energy and radiation may also be utilized to activate or enhance the activity of drugs and active agents which have been introduced into the ductal lumen(s). For example, ultrasonic energy may be used, e.g., to excite a fluid or material that is inside the duct. The fluid or material can then act upon the duct, including the ductal lining. For example, polymers which are sensitive to ultrasonic energy can be administered to a breast duct. The present invention provides intraductal delivery of the polymer spheres, and localized or intraductal exposure of the duct or breast to ultrasound to achieve the diagnostic or therapeutic purpose. If the polymers are beads that house a cavity, the cavity can be filled with a diagnostic or therapeutic material which is delivered to the breast duct. When exposed to ultrasonic energy the polymer wall breaks down and the bead disperses the material that was carried inside the polymer. Such beads are available from Point Biomedical located in San Carlos. See website.

Photodynamic therapy (PDT) may be practiced by intravenous (systemic) delivery or intraductal delivery of a photoactivatable material followed by exposure to light that activates the material. In this invention, a PDT drug, such as, for example, Lutex is delivered via catheter into one or more mammary ducts. At the desired time, light of the appropriate frequency is applied to the outer surface of the breast or intraductally using a fiber optic. The most desirable frequencies of light are in the range of 700 nm to 800 nm which is the range that provides the highest penetration depth in tissue and blood. The light activates the PDT drug and the therapeutic effects begin after the drug is activated.

The invention also provides for the delivery of radiosensitizers that enhance radiation treatment. A radiation sensitizer can be administered to the duct or systemically. The sensitizer can be, for example, gadolinium which goes through an electron reduction forming a free radical when exposed to x-ray or gamma radiation. Texaphyrin can be combined with gadolinium to form a metallotexaphyrin (see U.S. Pat. No. 5,801,229) which is available from Pharmacyclics, Inc. The toxicity of gadolinium is further increased when exposed to the gamma or x-rays. The radiation sensitizer need not be metallic-based, but may also be a drug or chemical which enhances a cell's susceptibility to radiation, such as CMNa (a nitroimidazole compound, see U.S. Pat. Nos. 5,650,442, and 4,820,844), carboplatin (see U.S. Pat. No. 5,780,653), or gemcitabine.

Radioisotopes can be delivered to the duct. A radioisotope can be delivered alone or conjugated to an antibody that is specific for a tumor or lesion antigen. The antigen can be, for example, a ductal epithelial cell surface molecule, or a cell surface protein that is expressed on the surface of transformed, cells. The radioisotope can be conjugated to a monoclonal antibody which is capable of targeting breast ducal epithelial cell epitopes, e.g., the antibodies HER2 (see Ross and Fletcher, *Oncologist* 3(4):237–252 (1998); Pegram et al., *Oncogene* 18(3):2241–51 (1999)) or MUC1 (Chu and Chang, *Cancer Lett* 142:121–7(1999); Goldenberg and Nabi, *Semin Nucl Med* 29:41-(1999)). The radioisotope can be a particle emitting isotope, e.g., an alpha particle emitting radioisotope, e.g., Bismuth-213 (Bi-213). Alpha emitting radioisotopes are preferred because alpha particles have a short penetration depth (typically 3–6 layers of cells), are easily shielded, the present minimal radiation risks during handling. The alpha particles generated during the degradation of Bi-213 are particles with sufficient energy to ablate a limited radius of cells in the ductal lumen and surrounding the duct (e.g., myoepithelial cells, basal cells or stromal cells), and has a short half-life, about 45 minutes. Additionally, Bi-213 decays into stable Bi-209 which is approved for use in humans (and is biocompatible) and is routinely used in pharmaceuticals. To target specific lesions identified in a duct, any atypical ductal cells retrieved from a duct can be tested for antigens, and an appropriate antibody conjugated to the Bi-213 molecules for administration into the duct and specific targeting to the lesion.

Heating the breast duct (and/or fluid in the duct) may be provided in a number of ways. Heating the duct may be provided by intraductal access of a laser equipped ductal access tool for generating enough laser energy intraductally to ablate the ductal lumen tissue, including any lesions present in the duct. Preliminary work by radiologist Steven Harms at University of Arkansas has shown that laser ablation of tumors is possible and effective. Additionally, laser heating to ablate breast lesions is described in Robinson et al., *J Am Coll Surg* 186(3):284–292 (1998).

Radiowaves at particular frequencies or microwaves may be used to preferentially heat a medium in the breast ducts and thus ablate the ductal tissue but not other breast tissue distal from the duct. For example a fluid or material with a resonance frequency of that of an electromagnetic source (e.g., radiofrequency and microwave, etc.) can be administered to a breast milk duct. Upon application of the electromagnetic energy (either intraductally, or to the entire breast) the fluid or material in the duct with the resonance frequency that corresponds to that of the electromagnetic source would resonate the heat. The heat would destroy the ductal system that contains the resonating fluid or material. The amount of heating is controlled by the amount of electromagnetic energy applied. Metallic fluids such as gold or silver colloid can be used, for example, as the fluid or material placed into the duct to resonate at a particular electromagnetic frequency.

Microwave heating of the breast duct can also be accomplished with a breast duct access tool capable of generating a local heat that affects only the lesion and surrounding tissue of the ductal lumen. A company called Celsion, located at Columbia, Md., is developing this particular version of hyperthermia therapy. The methods are described for application in broken tissue, whereas the present invention provides methods to apply the ablative therapy intraductally..

The present invention still comprises removing energy from the cellular lining of the duct, e.g., freezing the cellular lining, using cryogenic apparatus and methods. Agents of extreme cold, or agents which draw heat from surrounding tissue that contact the agent can be applied locally to the breast duct using a cryo-probe adapted for ductal access to ablate a lesion in the duct or other luminal tissue. A company called Endocare, Inc. is developing a CRYOcare 1-Probe Surgical system for administration to surgical incision sites. The Endocare product may be adapted for administration to an accessed breast duct instead of a surgical site. Extreme cold is applied through administration of a cryo agent to the ductal lumen resulting in an ablation of the ductal tissue that contacts the agent. See website for more information about this procedure generally. See also article by Brown, *J. Nat'l Cancer Inst.* 90(5):351–353 (1998).

Additionally, Titan Corp. of San Diego and TomoTherapeutics has developed an x-ray needle its subsidiary. More information about the tool and therapy is found on the internet at. The tool may be applied or modified for use intraductally, to therapeutically ablate ductal tissue comprising a lesion.

Brachytherapy has been described to treat local breast disease. The brachytherapy described can be modified for administration intraductally, without incision or tissue removal. Dr. Robert Kuske is completing work along these lines at Ochsner Clinic in New Orleans, La., as described by Reuters Health Information web report Nov. 9, 1999, website.

Finally, radiofrequency (RF) therapy can be applied intraductally. A ductal access tool capable of delivering radiofrequency waves can be introduced into a breast duct and radiofrequency waves can be delivered to the duct to ablate tissue into a ductal lumen, including any lesion.

In a first specific aspect of the present invention, a method comprises selecting an individual duct and transferring energy to or from cells lining the duct in an amount sufficient to destroy or inhibit proliferation of said cells. The individual duct is usually selected based on a prior diagnosis or evaluation of that duct indicating a presence or risk of DCIS or other cancer within the duct. Particular methods for accessing individual ducts through an associated orifice in the nipple and for diagnosing abnormal conditions within the duct are described in prior application Ser. Nos. 08/931,786, 09/067,661, and 09/301,058, the full disclosures of which have previously been incorporated herein by reference. Briefly, at least one and usually all ductal orifices in the nipple of a breast are first located and marked using localization techniques. The lumens of each of the ductal networks can then be accessed using small diameter catheters which permit collection of cellular and other materials. By evaluating the cellular and other materials which are collected, the presence or risk of disease within an individual ductal network can be evaluated. Those individual ducts which are diseased or at risk of disease can then be selected for treatment according to the methods of the present invention.

While it will frequently be desirable to locate and screen all of the ductal orifices as just described, in certain cases it will be necessary to screen only pre-selected ductal orifices, e.g. those which display indications suggesting that they may be pre-cancerous or otherwise of particular interest. For example, it may be possible to identify regions of the breast or even particular ductal orifices which have conditions such as calcification indicating that only certain ductal orifices need to be screened. In some instances, it may even be possible to identify particular ductal networks and associated network orifices for treatment by the methods of the present invention without performing a specific ductal screening technique, e.g. using mammography, ultrasound, magnetic resonance imaging (MRI), or other ductal non-specific screening technique.

Depending on the nature of the diagnosis, the entire ductal network or only a portion thereof can be treated. To treat a portion of the ductal network, the transfer of energy will preferably be limited to the cells lining only that portion. Usually, however, it will be desirable to treat substantially the entire ductal network and energy will be transferred to or from the cells lining the entire ductal lumen.

When applying high frequency or other forms of electrical energy to the ductal lumen, it will usually be desirable to first introduce an electrically conductive medium, such as saline, electrically conductive contrast medium, or the like, to substantially fill (and usually distend) the entire duct. Methods utilizing dual lumen catheters for flushing and filling ductal networks are described in co-pending application Ser. Nos. 09/067,661 and 09/301,058. Once the ductal network has been filled with the electrically conductive medium, an electrode or other electrically conductive member can be introduced to the lumen, typically through the ductal orifice, and current flow established through the conductive medium to reach substantially all portions of the cellular lining. In the case of radiofrequency and other electrical energy treatments, a "monopolar" energy or current flow will usually be established. That is, the electrically conductive medium within the ductal network will be connected to one pole of a suitable radiofrequency or other power supply, while the other pole is connected to a dispersive electrode which is placed on the patient's skin, preferably over at least a portion of the breast, and more preferably over a region which circumscribes the breast. Alternatively, the dispersive electrode can be placed on the patient's thigh, or over the lower back, percutaneously with the breast tissue, or in any other manner typically used in monopolar electrosurgical procedures.

Electrical energy could also be applied in a bipolar fashion with a first pole spaced-apart from a second pole within the lumen. In that way, electrical energy could be focused with a well defined length of the lumen.

While electrical energy will usually be delivered into the electrically conductive medium within the ductal network directly using electrode(s), it will also be possible to selectively heat the medium within the ductal network using radiofrequency induction. A radiofrequency antenna or other source, optionally shaped to conform to the exterior of the breast, may be used to selectively excite and heat the conductive medium which has been delivered into the breast. As breast tissue is primarily water, such conductive heating will generally be useful to raise the ductal temperature to very high temperatures, but rather be useful to selectively increase the temperature relative to the rest of the duct to inhibit cellular proliferation. Energy may also be transferred to the breast by introducing energy active species, such as photodynamic species, followed by a subsequent treatment of the breast using ultraviolet or other light or radiation having a wavelength selected to excite the introduced photodynamic or other species. It will be appreciated that the present invention is directed at the ductal-specific delivery of energy to the ductal network and may comprise a wide variety of specific techniques for such delivery.

The agent can comprise an agent sensitive to vibrational energy, for example, collagen spheres that break-up upon a diagnostic level of ultrasound applied to the breast or ductal lumen.

The energy will be applied in an amount and over a time sufficient to at least inhibit cellular proliferation of cells lining the ductal lumen, usually epithelial cells lining the lumen. More usually, the energy will be applied in order to necrose all cells lining the ductal lumen. Usually, at least the inner layer of epithelial cells which line and are directly exposed in the ductal lumen will be effected, usually being destroyed. Often, it will be further desirable to treat and usually destroy an epithelial layer below the first layer, and in some instances it may even be desirable to destroy the myoepithelial layer or beyond. The electrical energy will typically be applied at a power level from about 50 W to 300 W, usually from about 120 W to 200 W. The power may be applied continuously, or may be applied at a duty cycle typically in the range from 10 percent to 90 percent, often from 25 percent to 75 percent. Optionally, the amount of power delivered can be controlled based on preselected algorithms and/or feedback control algorithms. For example, the amount of power delivered to the duct could be controlled based on the temperature of the ductal lining, the temperature of the electrically conductive medium within the duct, electrical impedance between electrodes, or other measured values taken during the treatment protocol.

In addition to various forms of electrical energy, the present invention may provide for delivery of other forms of radiation, including electromagnetic, ultraviolet, infrared, nuclear, x-ray, and the like. In particular, nuclear radiation can be delivered using a solution, dispersion, sol, seeds, or other form of radio isotopic medium which can be introduced into and throughout the ductal lumen, typically using a syringe, a infusion catheter, or other device. Nuclear radiation may also be delivered to the ductal lumen using a radioactive catheter, wire, stent, implantable seed, or the like. Catheters may be designed to immobilize a nuclear radiation source, where the source may then be advanced through the ductal lumen to selectively expose portions of the luminal wall. Alternatively, or additionally, catheters may provide delivery paths for introducing nuclear materials, where the materials may be transported within the catheter to provide the desired treatment times and regions. Infrared and ultraviolet radiation may be delivered using suitable light fibers and other optical systems. X-ray energy can be delivered using a miniaturized x-ray source which can be introduced and translated through at least selected portions of the ductal lumen system.

Systems according to the present invention for applying high frequency or other electrical current to a breast duct comprise a lumen electrode, a dispersive electrode, and optionally conductive fluids to be introduced into the ductal network. The lumen electrode will be adapted to enter a lumen of the duct, typically through the associated ductal orifice, but alternatively percutaneously through tissue into the duct. The lumen electrode may be a simple single wire or filament electrode, with the primary requirement being the ability to carry sufficient power to the ductal lumen, i.e., within the power ranges set forth above. The dispersive electrode will be adapted for placement on and conformance to a region on the patient's skin, usually on the breast, more usually circumscribing the breast, but alternatively on other locations, such as the lower back, thigh, abdomen, or the like. The system may further comprise a sheath having a lumen for introducing the lumen electrode through the ductal orifice. The sheath will typically be composed of an electrically insulating material, and the electrode will be advanced out a distal tip of the sheath in order to contact the electrically conductive medium that has been introduced to the ductal lumen, as described above. Suitable electrically conductive fluids include saline, Ringer's medium, lactate solution, and other physiologically acceptable electrolyte. Usually, from 0.1 ml to 10 ml, typically 0.5 ml to 5 ml will be introduced into a single ductal network, and systems and kits may include vials, syringes and other containers holding pre-measured amounts of the conductive fluids. Optionally, the system may further comprise a high frequency electr pole for connection to the lumen electrode and a second pole for connection to the dispersive electrode. The power supply may incorporate control features to implement the control protocols described above.

The present invention further comprises kits for treating a breast duct. The kits will usually comprise a probe, such as a lumen electrode, and optionally a dispersive electrode and conductive fluids as just described. In addition, the kits will include at least instructions for use, usually in a printed format, more usually being printed on a separate piece of paper packaged together with the kit, or printed on a portion of the kit packaging. The instructions will set forth a method for treating a breast duct as generally described above, where the probes used to transform energy to or from the duct. The kit may further comprise a suitable package, usually in the form of a pouch, tray, box, tube, or other conventional package structure. Usually, although not necessarily, at least the electrode component of the kit will be sterilized and maintained in a sterile condition within the kit, e.g., usually being maintained in a sterile package or sterile portion of the package. The instructions for use may set forth any of the protocols set forth above in connection with the description of the methods of the present invention.

While the present invention is particularly useful for delivering energy to the ductal network in an amount and for a time sufficient to destroy at least a portion of the epithelial or other cellular lining of the ductal lumens, as described above, the invention will also find use in treating cancers and other conditions which extend beyond the cellular lining of the ductal network.

BRIEF DESCRIPTION OF THE DRAWINGS

FIGS. 7A–7D illustrate a photodynamic therapy for ablation of the ductal epithelium.

DESCRIPTION OF THE SPECIFIC EMBODIMENTS

Figure 1:
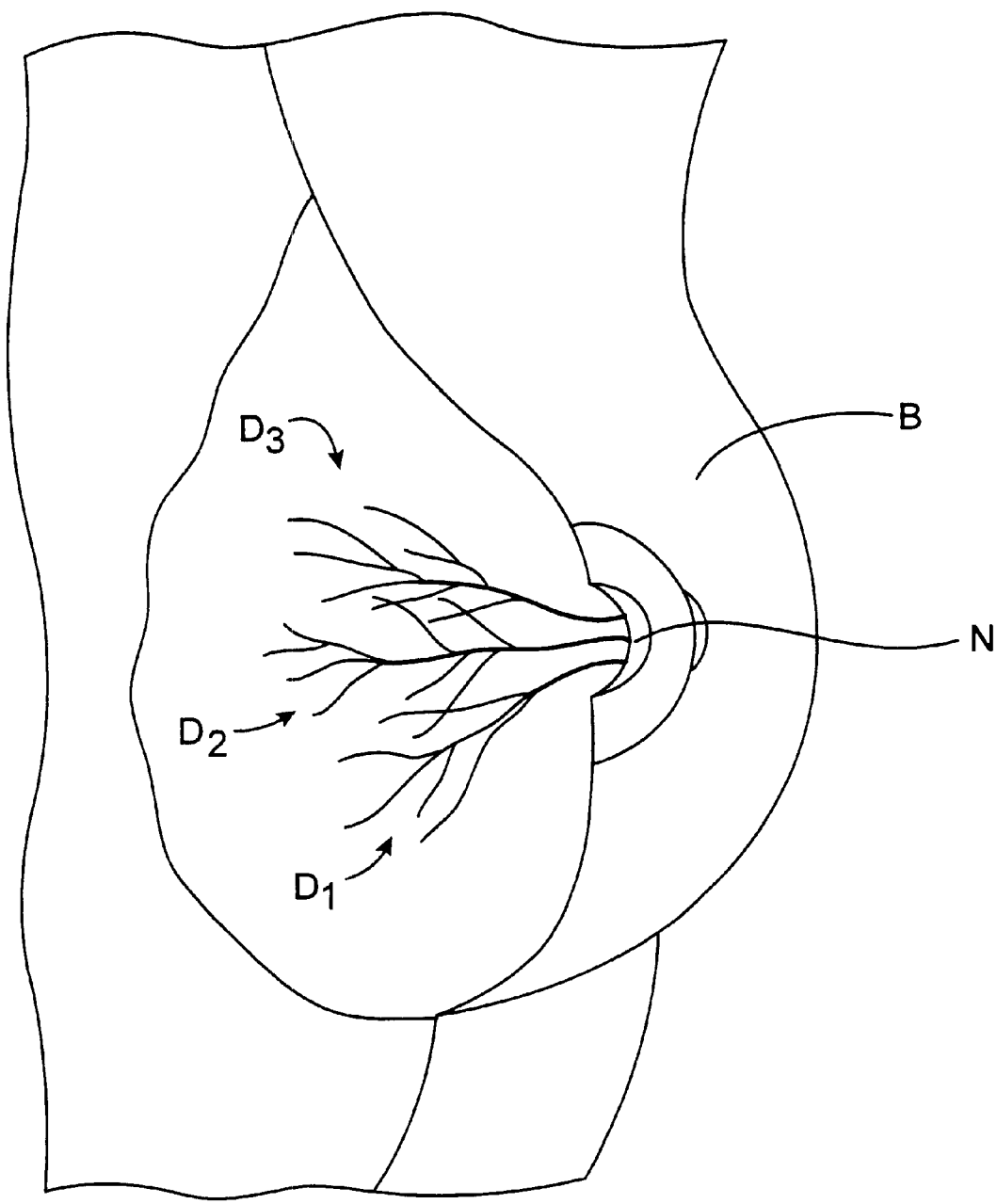
FIG. 1 is an anterior view of a human female breast, shown in section, and illustrating three of the six to nine ductal networks extending inwardly from the nipple.
Figure 2:
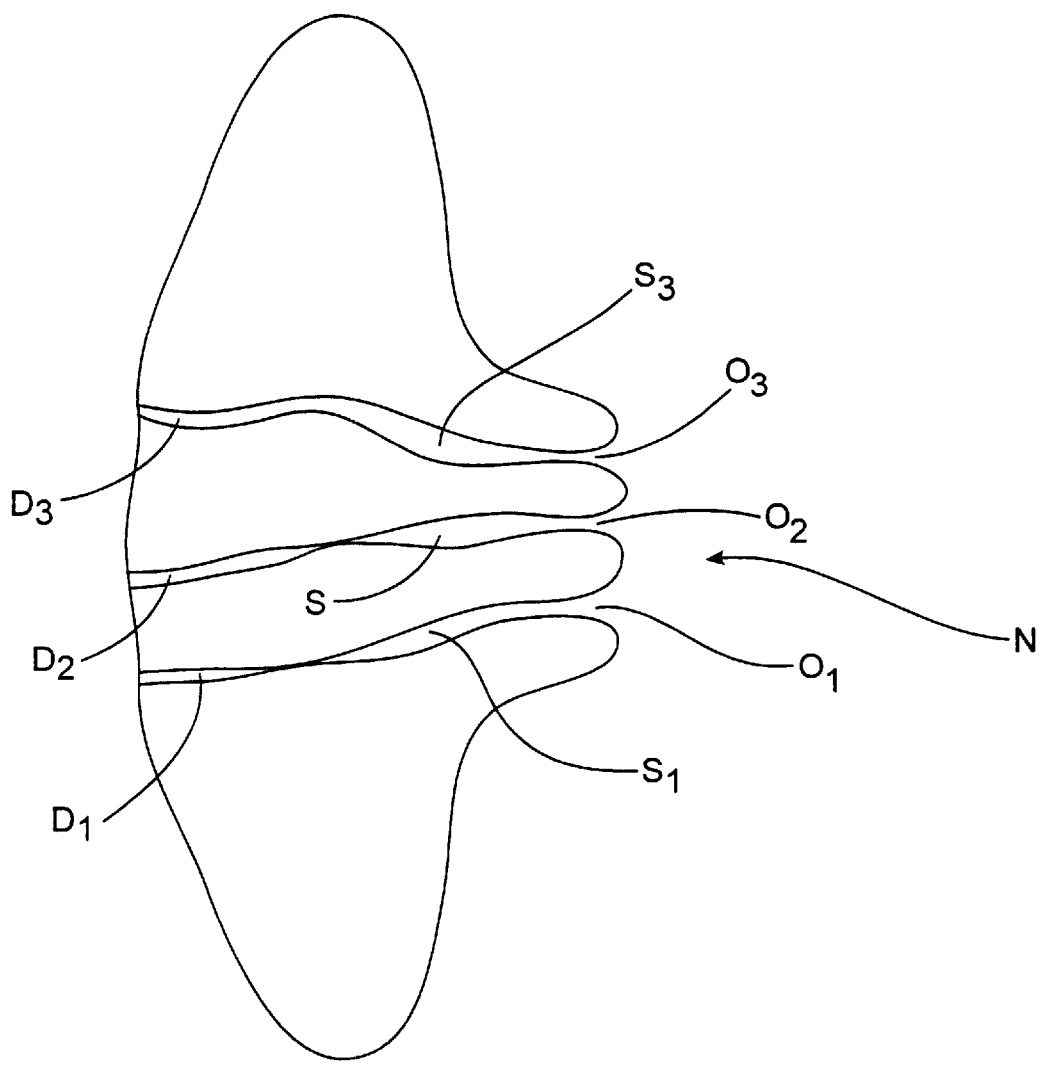
FIG. 2 is an enlarged view of the nipple of FIG. 1 illustrating the orifices leading to each of the three ductal networks.

The present invention comprises methods, systems, and kits for treating the cellular linings of ductal networks in a human or animal breast. A typical breast B, as illustrated in FIG. 1, includes a nipple N and from six to nine ducts D. Three ductal networks $D_{1-3}$ extending inwardly from the nipple N into the breast tissue are illustrated. As best seen in FIG. 2, each ductal network $D_{1-3}$ begins with an orifice $O_{1-3}$ which lies at the surface of the nipple N and extends inwardly through a ductal Sinus $S_{1-3}$ and then into a branching network. Each network D comprises a series of successively smaller lumens which are arranged in complex, three-dimensional patterns. The networks of each duct will overlap within the breast tissue but will not be interconnected. The total volume of each network is usually in the range from 0.1 ml to 0.5 ml, but the walls are somewhat compliant so the internal volume may increase as fluid is introduced. The treatment methods of the present invention generally rely on accessing the ductal network(s) through the orifice O of the duct D within the nipple N. Usually, there will be from six to nine orifices which open into a like number of ductal networks. If desired, confirmation of the number and location of the ductal orifices for any individual patient can be made by labeling the nipple as described below.

The therapeutic methods of the present invention will usually be performed following a diagnosis or evaluation of cancer or a pre-cancerous condition or other disease in one or more of the duct(s) of the patient. In some cases, however, the methods could be used prophylactically in asymptomatic patients at significant risk of cancer or other breast diseases. The manner of making a diagnosis does not form part of the present invention and may be performed as described in earlier application Ser. No. 09/067,661, and CIP application Ser. No. 09/301,058, the full disclosures of which have been previously incorporated herein by reference. Briefly, such diagnosis of individual breast ducts relies on collecting endogenous ductal fluids and cellular and non-cellular marker materials from the individual ductal networks on a duct-by-duct basis. That is, fluids and marker materials are obtained from a single duct without obtaining material from any other ducts. This is in contrast to other techniques which, in some instances, are able to obtain cellular and other materials from all milk ducts at once by applying a mild vacuum to the nipple. It should be noted, however, that in some instances such screening of all ducts in a single step may be appropriate in order to identify patients showing abnormalities for whom further, duct-specific testing is appropriate. Other identification techniques may also be employed. For example, calcification may be identified using mammography followed by duct-specific diagnosis to confirm the identity of the associated duct and to confirm that the calcification are associated with DCIS or other abnormal conditions.

In order to carry out the diagnosis, a location of at least one duct will be determined, typically by labeling at least one and usually all ductal orifices as described in co-pending application Ser. No. 08/931,786, the full disclosure of which has previously been incorporated herein by reference. Briefly, a portion of the epithelial lining present exposed at the ductal orifice may be labeled with a visible marker which allows the treating professional to identify the entry orifice for each of the ductal networks in the breast. Following identification of the ductal orifice, a washing fluid will be introduced into the duct in order to loosen and mobilize cellular material from the ductal lining, primarily epithelial cells from the lining. The washing fluid is introduced in an amount and a manner such that substantially the entire volume of the duct will be washed with the fluid in order to obtain a sample which is representative of the entire ductal network. Cellular components from the sample will usually be of the most interest, but ductal fluids and secreted molecular species (both small molecules and more usually biological macromolecules such as proteins and carbohydrates) may also be analyzed. The washing fluid carrying the cells and other materials is then collected, and the materials morphologically, (i.e., cytologically), histologically, immunohistologically, chemically, immunologically, enzymatically, or otherwise examined in order to determine any abnormal or disease conditions within the ductal network, particularly cancer or a precancerous condition.

Figure 3A:
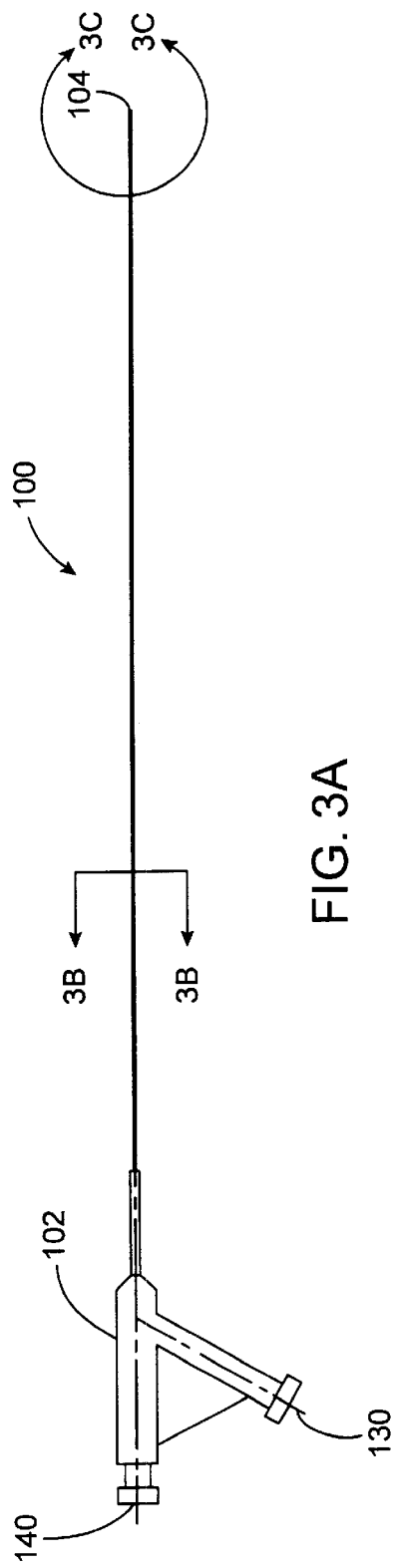
FIGS. 3A–3C illustrate a catheter suitable for accessing and diagnosing an individual ductal network as well as for introducing an electrode for high frequency energy therapeutic treatment according to the method of the present invention.
Figure 3C:
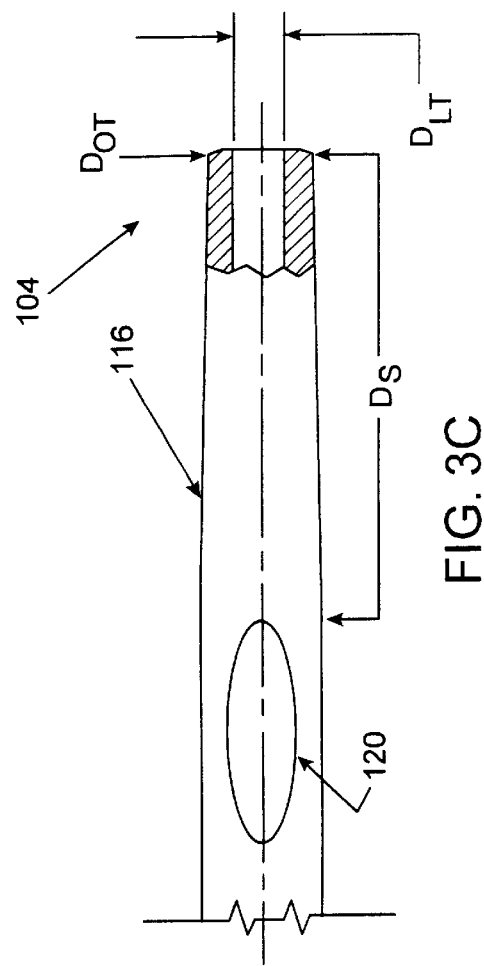
Figure 3B:
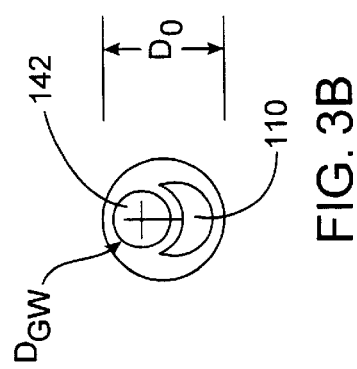

An exemplary catheter 100 suitable for accessing ductal lumens for both diagnosis and therapy according to the present invention is illustrated in FIGS. 3A–3C. The catheter 100 is a three French double lumen catheter with a length from hub 102 to distal tip or port 104 of about 30 cm, and outer diameter $D_O$ (FIG. 3B) of about 1 mm, a guidewire $D_{GW}$ of about 0.5 mm, and a crescent-shaped lumen 110. The outer tip diameter $D_{OT}$ is about 0.8 mm and the luminal tip diameter $D_{LT}$ is about 0.4 mm, with the distal end 116 being tapered. A sideport 120 having an oval geometry opens from the crescent-shaped lumen 110 and is spaced proximally of the tip 104 by a distance $D_S$ of about 4 mm. Fluid for washing the duct is introduced through port 130 into the lumen 110 and out through the side port 120 into the ductal lumen. Fluid may be collected through port 140 on the hub 102 via the guidewire lumen 142 which extends to the distal tip 104. The catheter may be formed from a wide variety of polymeric materials which possess sufficient flexibility and hoop strength, such as polyethylenes, polyimides, and the like. The particular dimensions and geometry set forth above have been found to be suitable for accessing and diagnosing the breast and would further be suitable for introducing an electrode into the ductal lumen, as described in more detail hereinafter. Other catheters suitable for the task are described in co-pending application Serial Nos. 60/143,359 and 60/143,476, both filed Jul. 12, 1999, the disclosures of which are hereby incorporated by reference in their entirety.

Figure 4A:
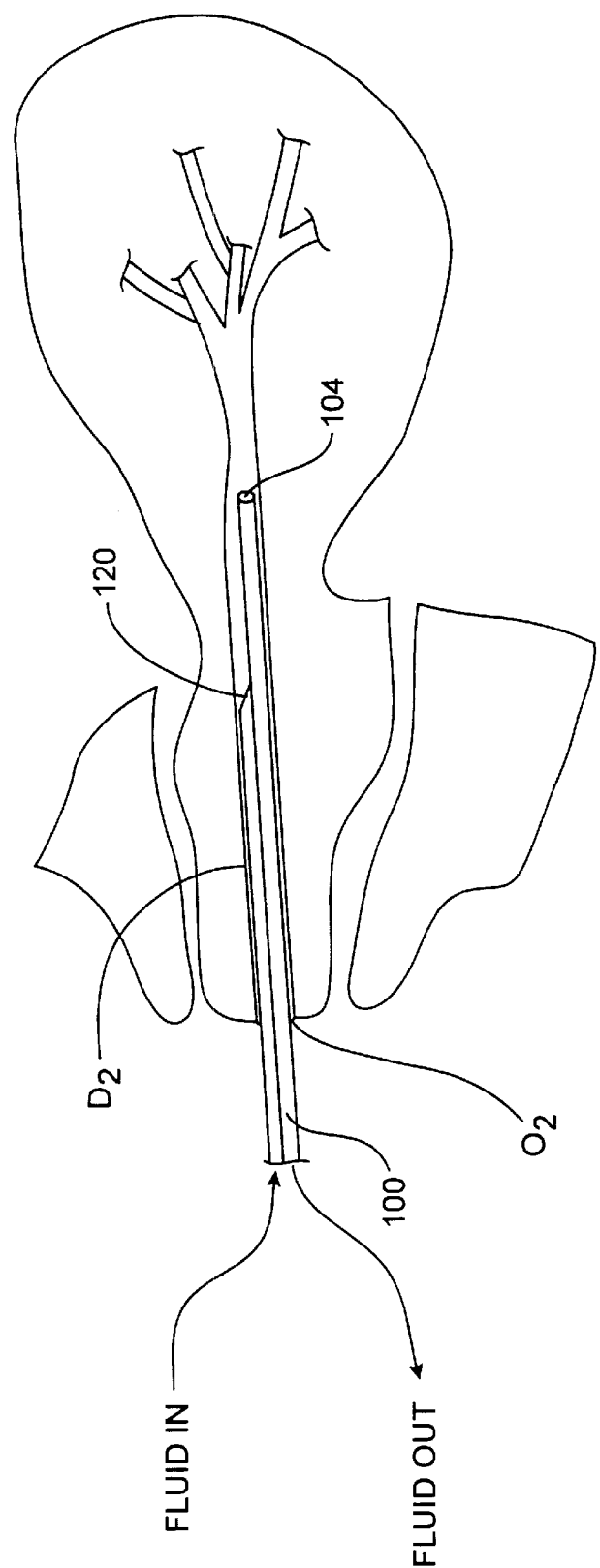
FIG. 4A illustrates use of the catheter of FIG. 3 for accessing and diagnosing a ductal lumen as a preliminary step to performing the therapeutic treatment of the present invention.

As illustrated in FIG. 4A, the catheter 100 is used for collecting the cellular and other marker materials from a ductal network $D_2$ by first accessing the duct with a guidewire, such as a conventional 0.014 inch guidewire (not shown). After the guidewire is introduced, typically by a distance in the range from 0.25 cm to 2.5 cm past the orifice $O_2$, the catheter 100 will be introduced over the guidewire by passing the distal port 104 thereover. The distal port 104 is introduced, also typically to a depth from about 0.25 cm to 2.5 cm, usually from about 0.5 cm to 1.5 cm. Fluid is first introduced through port 120 to substantially fill and slightly distend the ductal lumen, typically at a gauge pressure from 1 psi to 20 psi. The fluid may then be collected through distal port 104. Typically, fluid will be recirculated continuously from the port 120, through the ductal network, and then collected into the distal port 104. Particular techniques and alternative techniques for performing the washing and analysis of the ductal lumens is described in co-pending application Ser. Nos. 09/067,661 and 09/301,058.

Figure 4B:
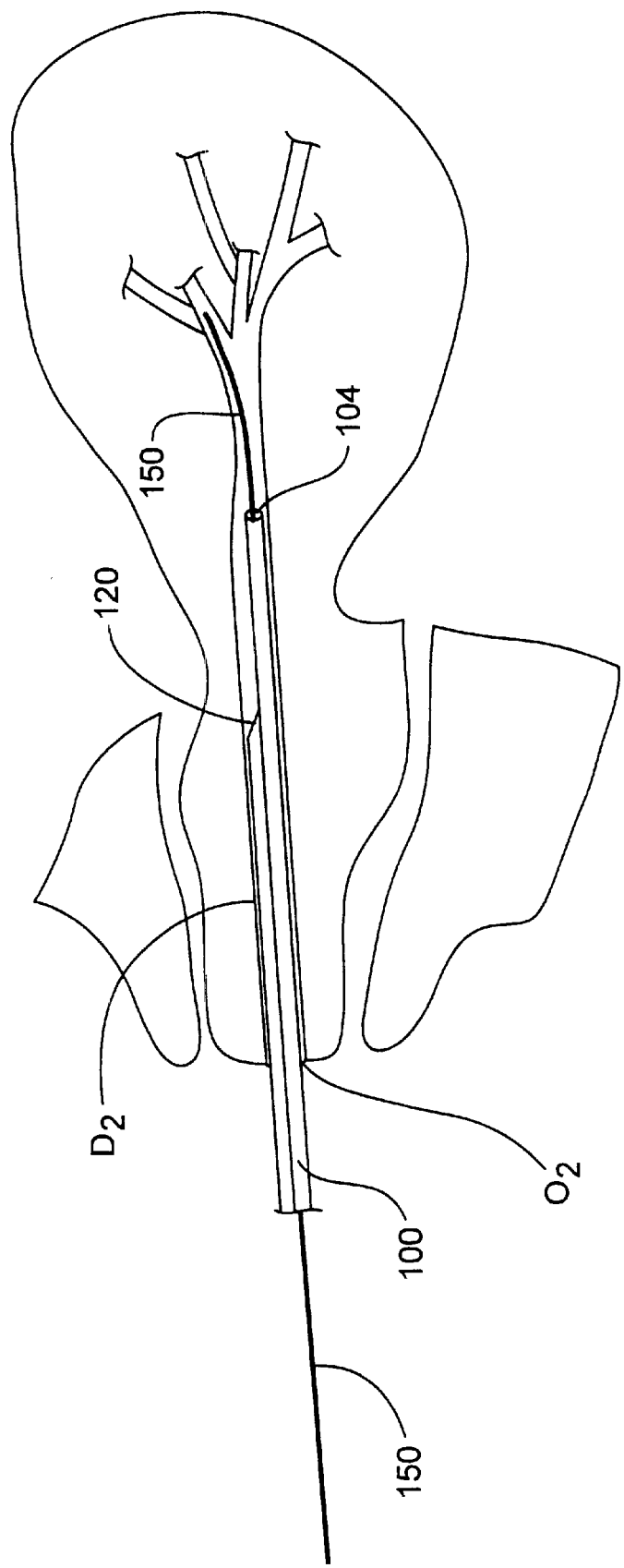
FIG. 4B illustrates use of the catheter of FIG. 3 for introducing an electrode for performing high frequency electrical treatment according to the methods of the present invention.

After the diagnosis is complete, the methods, systems, and kits of the present invention may be used to treat individual ductal lumens which are diagnosed as having cancerous, pre-cancerous, or other abnormal cells or disease conditions. A preferred method for treating the duct $D_2$ is illustrated in FIG. 4B. A sheath or other cannula which may be the catheter 100 described above, is reintroduced to the duct $D_2$, usually to a depth substantially equivalent to that used for diagnosis. A luminal electrode 150 is then introduced through the guidewire lumen so that it extends distally of proximal port 104 into the ductal lumen. Before or after introducing the electrode, an electrically conductive medium will be introduced to substantially completely fill the entire ductal network. Unlike the diagnosis step, however, the fluid will typically be maintained in a static condition, i.e., without recirculation. Usually, a slight static pressure will be maintained on the fluid in order to completely fill and slightly distend the ductal network, typically at least about 1 psi, often at least about 3 psi, and sometimes 5 psi or higher.

Figure 5:
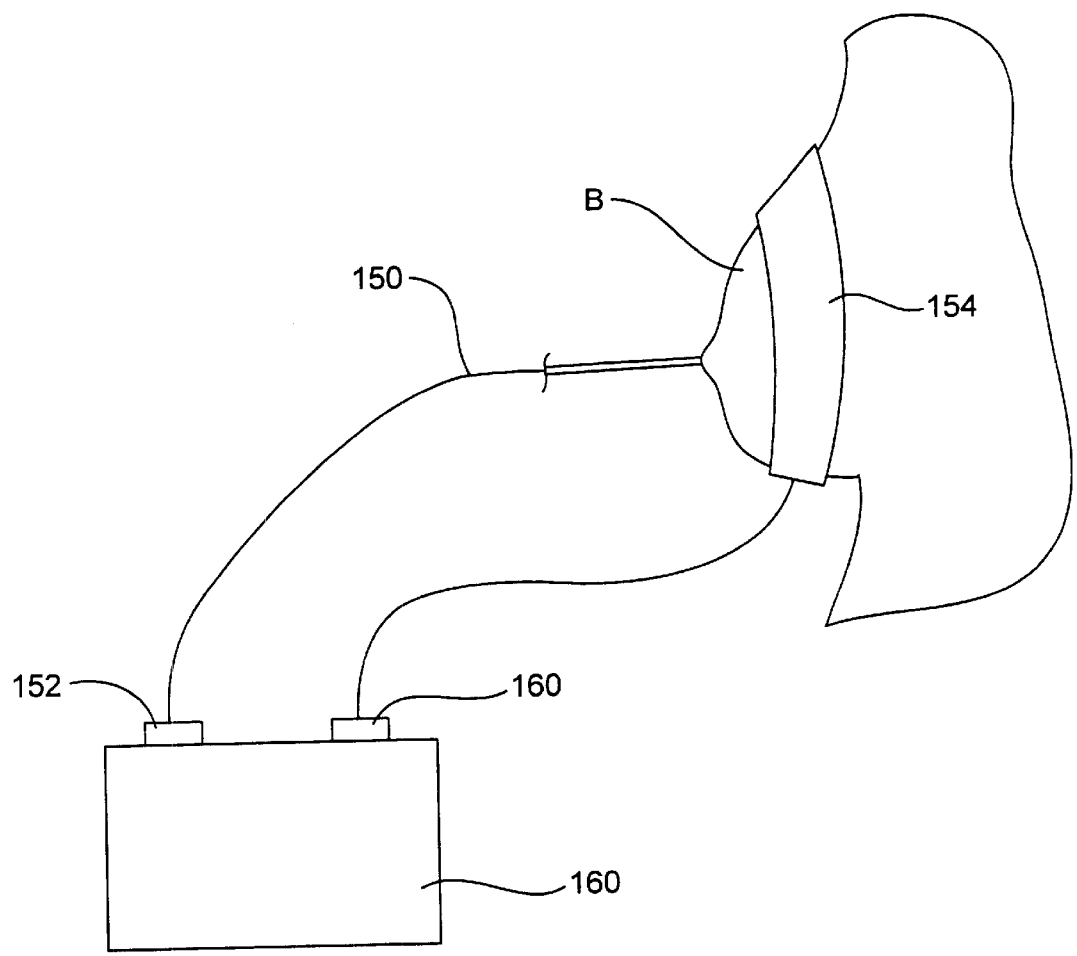
FIG. 5 illustrates a system according to the present invention in use during a therapeutic treatment.

Referring now to FIG. 5, the electrode 150 may be connected to a first pole 152 of a high frequency power supply, such as a conventional electrosurgical power supply. A dispersive electrode 154 may be placed about the exterior of the breast B, typically circumscribing the breast, as illustrated in FIG. 5. The dispersive electrode will be connected to the other pole 156 of the power supply 160. Suitable electrosurgical power supplies are available from a number of commercial vendors, such as Valleylab, Aspen, Bovie, and Birtcher. The power supply will usually provide energy at high frequencies in the range from about 200 kHz to 4 MHz, and may employ conventional sinusoidal or non-sinusoidal waveforms. The total power delivered to each ductal lumen may be in the range from 50 W to 300 W, usually from about 120 W to 200 W. The electrical energy will be applied for a time sufficient to inhibit proliferation of the cells lining the breast duct, usually for a time sufficient to ablate or necrose substantially the entire cellular layer lining the breast duct.

As illustrated in FIG. 5, operation of the electrosurgical system is "monopolar." That is, the current flows between the lumen electrode, which is considered an active electrode to the dispersive electrode disposed on the exterior of the patient's skin. In other cases, it might be possible to perform the procedure in a bipolar manner. In such cases, two or more electrodes may be penetrated into the ductal lumen, where the electrodes are energized with opposite polarities. In some cases, at least one of the two electrodes might be introduced percutaneously, e.g., using a needle stick, into the breast tissue so that it is disposed at or near a distal terminus of the ductal network. In general, however, monopolar operation as illustrated in FIG. 5 will be preferred.

As described thus far, the electrically conductive fluid is directly energized by contact with at least a single electrode disposed in the duct lumen. It will also be possible to indirectly heat the fluid by inductive heating where an external antenna or electrode is brought into proximity with the breast and energized to excite and heat the fluid which fills the ductal lumen. Ultrasonic energy may be used, e.g., to excite a fluid or material that is inside the duct. The fluid or material can then act upon the duct, including the ductal lining.

Figure 6:
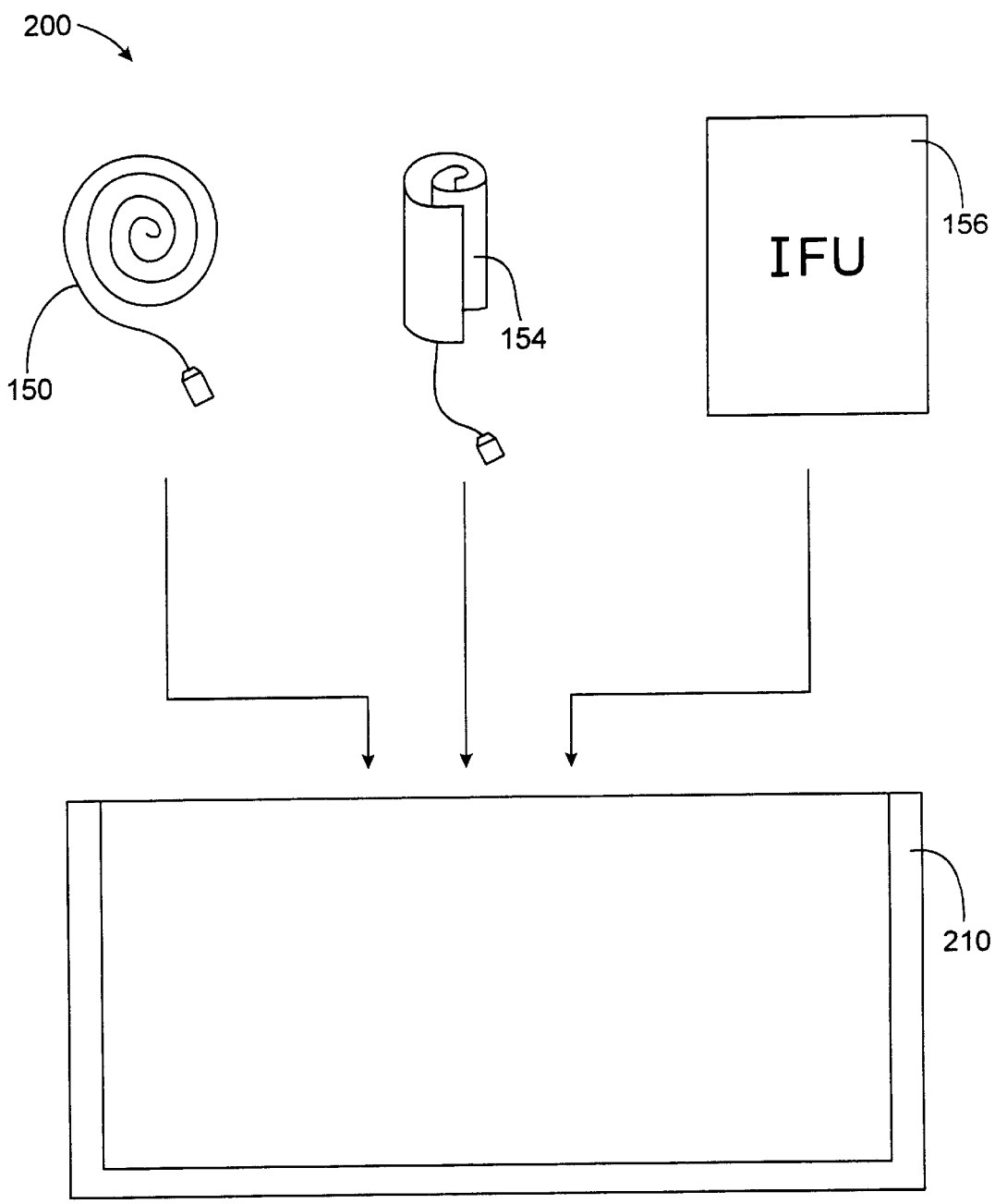
FIG. 6 illustrates a kit comprising a lumen electrode, a dispersive electrode, and instructions for use according to the methods of the present invention.

Kits 200 according to the present invention are illustrated in FIG. 6. The exemplary kit 200 comprises a lumen electrode, such as electrode 150, a dispersive electrode, such as electrode 154, and instructions for use 156 setting forth a treatment protocol for an individual breast duct according to the principals described above. The components of the kit will typically be packaged in a conventional medical device package, such as pouch 210, where some or all of the components may be maintained in a sterile environment.

Figure 7A:
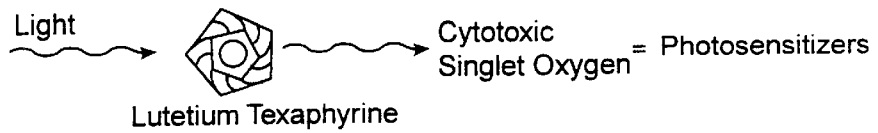
Figure 7C:
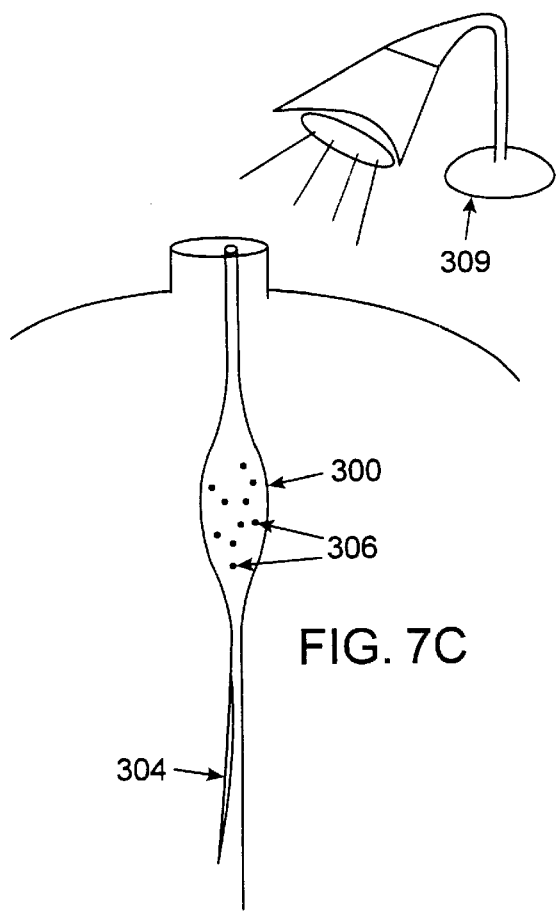
Figure 7D:
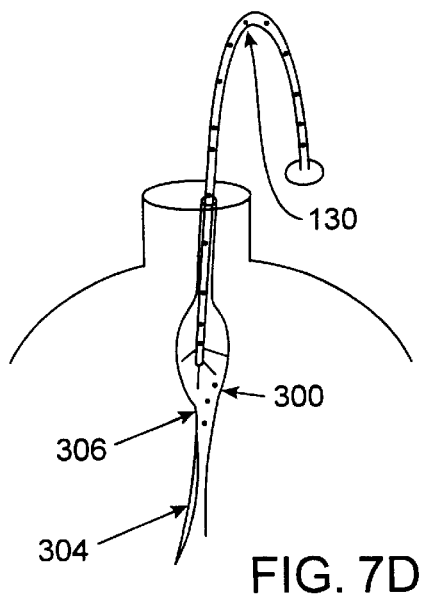

FIG. 7 depicts photodynamic therapy using light sensitive chemical (e.g., texaphyrins (porphyrins)) delivered locally to the breast duct, and applying the light source stimulation to the breast, either in the duct or at the breast generally. FIG. 7A depicts the chemical lutetium texaphyrin that after exposure to light emits cytotoxic signlet oxygen which attacks tumor cells. FIG. 7B depicts breast duct 300, nipple and breast 301, ductal orifice 302, and intraductal lesion 304. The duct 300 is accessed at the orifice 302 by catheter 307 containing a chemical 306, for example, lutetium texaphyrins in syringe delivery receptacle 308, delivered to the duct and contacting the lesion 304. FIG. 7C depicts the application of general light from a light source 309 to the external portions of the breast to excite the chemicals 306 in the duct 300. FIG. 7D depicts the application of an intraductally delivered light from a source 310 configured to access a breast duct 300 in order to excite chemicals 306 which in turn act on the lesion 304.

The device depicted in FIG. 7 may also be applied to administer a radiation sensitizer to a breast duct and activate it there. For example duct 300 is accessed at the orifice 302 by catheter 307 containing chemical 306, for example, the radiation sensitizer XCYTRIN, a metallotexaphyrin, can be administered to the duct in a syringe delivery receptacle 308, delivered to the duct and contacting lesion 304. An x-ray or gamma ray source is applied to the breast to activate the radiation sensitizer and provide toxic effects for intraductal tumor cells. The XCYTRIN molecules can capture electrons produced by x-ray or gamma radiation, resulting in one electron reduction of the complex. A pi (π)-radical cation is created that is reactive and capable of destroying neighboring biomolecules such as DNA. The radiation therapy is preformed by irradiation of the tumor site with x-rays or gamma rays (while shielding adjacent normal tissue to minimize toxicity). The x-rays and gamma rays interact with molecules in the duct such as water to generate high energy electrons and free radicals which are highly reactive and short-lived molecules. Radiation sensitizers are chemicals that increase the lethal effects of radiation when administered in conjunction with it. Tumor cells, which are hypoxic, are 2.3 to 3.0 times more resistant than normal cells to the damaging effects of ionizing radiation. Administration of XCYCLIN provides an agent of strong electron affinity capable of reacting with hydrated electrons to prevent them from neutralizing cytotoxic hydroxyl radicals, and thus promote radiation sensitization of hypoxic cells. Chemical 306 can comprise a chelating agent, such as e.g., ETPA or DTPA, to bind the metallic radioactive ions making them chemically inert, but still radioactive.

Figure 8A:
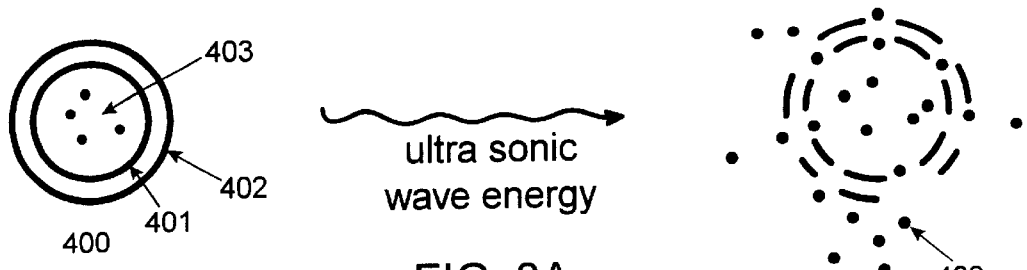
FIGS. 8A–8C illustrate ultrasound activation of biopolymers.
Figure 8B:
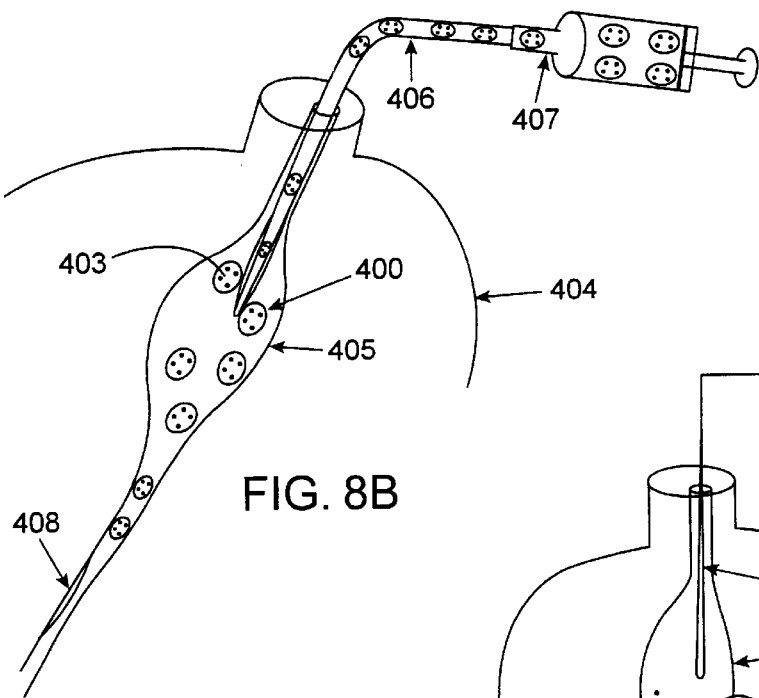
Figure 8C:
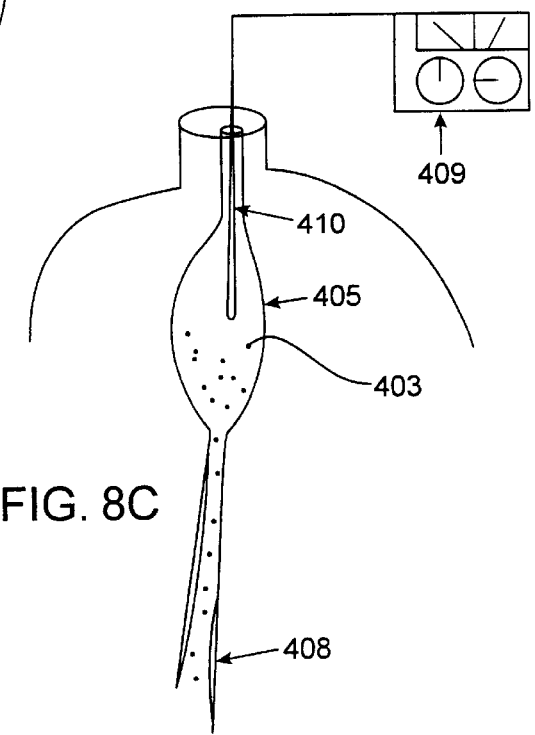

FIG. 8 depicts ultrasound activation of high molecular weight collagen derived biopolymers to better visualize the breast duct or to deliver diagnostic or therapeutic agents to the breast duct. FIG. 8A shows a polymer sphere housing either air or a diagnostic or therapeutic chemical 403. The sphere has an outer wall 402 and an inner wall 401 that can be designed to be sensitive to ultrasonic energy and to break open to release particles 403 as depicted. FIG. 8B shows a breast 404 containing a breast duct 405 and spheres 400 with particles 403 inside. The spheres are delivered in a ductal access tool 406 from a syringe delivery receptacle 407 in order to treat or diagnose lesion 408. FIG. 8C depicts the same duct 405 accessed by ductal access tool 410 having an ultrasonic signal transmitter connected to energy source 409. Lesion 408 is diagnosed or treated when particles 403 are released upon application of the ultrasonic wave energy.

FIG. 8C also depicts delivery of a fluid or substance that resonates at a particular frequency. Different mediums will resonate at different frequencies, and a medium selected to resonate at the frequency of applied radiofrequency or microwave energy will be preferentially heated over the surrounding breast tissue. In this embodiment, lesion 408 is ablated when medium 403 is delivered (for example, a gold colloid) to breast duct 405. Energy delivery tool 410 connected to energy source 409 supplies the radiofrequency waves or the microwaves that heat the medium preferentially and thus destroy some of the lining of the duct including the lesion 408. The resonant energy can also be applied externally to the outside of the whole breast and the effects of the energy would be felt where the medium was administered, i.e., in the target breast ducts.

Figures 9A, 9B:
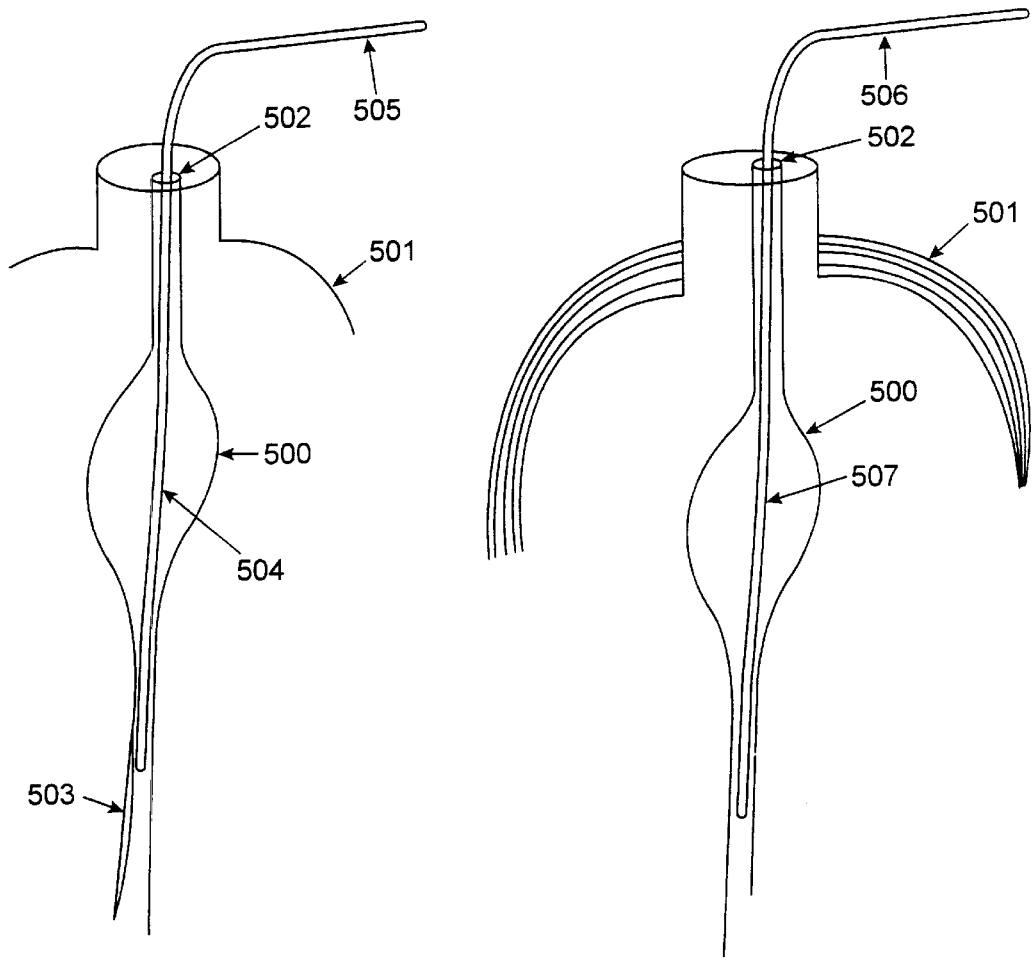
FIGS. 9A and 9B illustrate a ductal access device comprising fiber optic capacity.

FIG. 9 depicts a breast duct 500 in a breast 501 accessed by a needle containing ductal access tool 505 through orifice 502, so that fiberoptic light and energy source 504 can be threaded through the needle or lumen 505 to contact the lesion 503 and apply laser generated heat to the lesion. FIG. 9B shows the follow-up procedure to check that all the lesion is removed using a ductal access tool 506 with fiberoptic scope apparatus 507 placed into duct 500 in breast 501 to visualize that the lesion has been removed by laser-generated heat. See Robinson et al. *J Am Coll Surg.* 186(3):284–292, for details of the procedure with regard to systemic delivery of the ultrasonic sensitive agent and application of laser hyperthermia. A similar procedure can be performed using a cryo probe in place of the ductal access tool emitting laser-generated heat. Referring now to FIG. 9A, the cryo probe 504 is placed in the duct 500 and extremely cold temperatures are delivered to the duct and preferably contacting the lesion and killing the neoplastic cells of the lesion. The heat therapy can also be performed using a probe that delivers by microwave energy a concentrated heat that burns the ductal lumen including the lesion, but does not substantially damage other breast tissue.

Figure 10A:
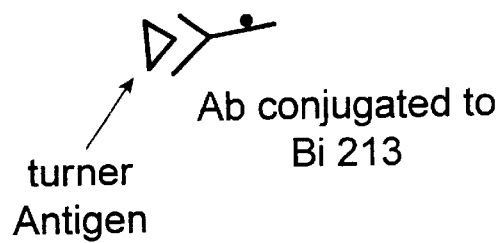
FIGS. 10A and 10B illustrate devices and materials for administration of a radioactive particle emitter.
Figure 10B:
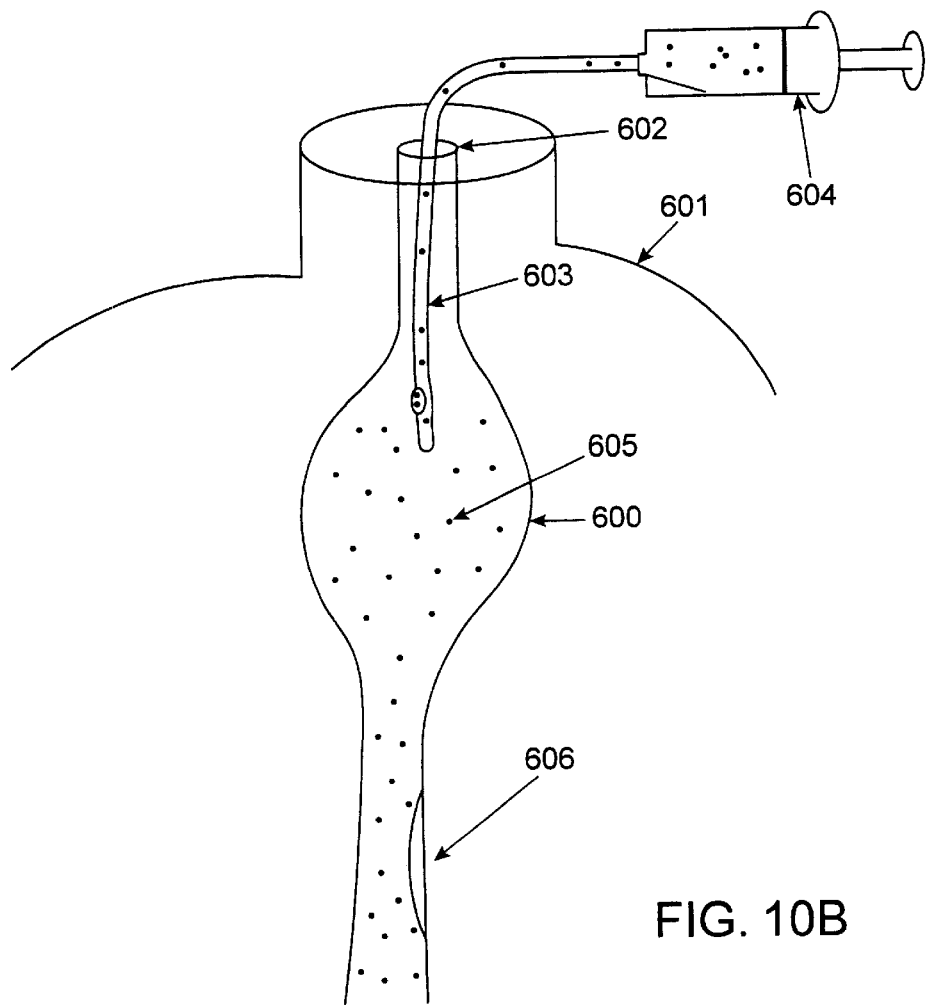

FIGS. 10A and 10B depict administration of a radioactive alpha emitter to the breast duct. The radioactive alpha particle emitter can be, for example, Bismuth 213 (Bi-213) (half-life 45 minutes), Bi-212 (half-life 60 minutes), Th-149 (half-life 4.13 hours), At-211 (half-life 7.21 hours), Fm-256 (half-life 20.1 hours), Ac-225 (half-life 10 days), and Ra-223 (half-life 11.4 days). Pure Bismuth 213 (Bi-213) may be coupled to an alpha particle emitter. FIG. 10A indicates Bi-213 conjugated to an antibody specific for a tumor antigen. Either the compound is administered to breast duct 600 in breast 601 by accessing the ductal orifice 602 with breast duct access tool and therapeutic drug administrator 603. The radioactive alpha emitter Bi-213 either alone or conjugated to a tumor or lesion specific antibody is contained in delivery receptacle 604 and administered through tool 603 from the receptacle. Inside the duct, the radioactive alpha emitter decays emitting an alpha particle capable of penetrating a cell wall and violating the integrity of a cell, including the hyperplastic or neoplastic cells of a tumor or lesion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating a breast duct, said method comprising:
    selecting an individual duct;
    positioning a device within said duct; and
    transferring energy to or from cells lining the duct in an amount sufficient to ablate or inhibit proliferation of said cells.

2. A method as in claim 1, wherein transferring energy comprises transferring energy substantially throughout an entire ductal network.

3. A method as in claim 1, wherein transferring energy comprises transferring energy within only a portion of the entire ductal network.

4. A method as in claim 3, further comprising identifying the portion of the ductal network to be treated, wherein energy is transferred only to that portion.

5. A method as in claim 1, wherein transferring energy comprises introducing energy to a lumen of the duct.

6. A method as in claim 5, wherein introducing energy comprises filling at least a portion of a ductal network with an electrically conductive medium and applying high frequency current to the medium.

7. A method as in claim 6, wherein from 50 W to 300 W of energy is applied.

8. A method as in claim 6, wherein applying the high frequency current comprises contacting the electrically conductive medium with an electrode that forms a portion of the device, and said method further comprises the steps of introducing the electrode through a ductal orifice and applying electrical current between the electrode and a dispersive electrode on the patient's skin or within a breast.

9. A method as in claim 8, wherein the dispersive electrode is disposed on the exterior of the breast.

10. A method as in claim 9, wherein the dispersive electrode is disposed circumferentially about the breast.

11. A method as in claim 1, wherein transferring energy comprises introducing a radiation source into the ductal lumen.

12. A method as in claim 11, wherein the radiation source comprises a radioisotope.

13. A method as in claim 11, wherein the radiation source comprises an X-ray source.

14. A method as in claim 1, wherein transferring energy comprises removing heat from at least a portion of an epithelial lining of an entire ductal network.

15. A method as in claim 14, wherein removing heat comprises introducing a cold fluid through the ductal network.

16. A method as in claim 14, wherein removing heat comprises introducing a fluid through the ductal network and thereafter freezing the fluid.

17. A method as un claim 1 wherein said device comprises an electrically conductive probe.

18. A method as in claim 17 wherein said electrically conductive probe comprises a lumen electrode.

19. An improved method for treating breast tissue comprising a step of applying energy to the breast tissue, wherein the improvement comprises:
   introducing a conductive medium into a breast duct; and
   wherein said applying step includes applying the energy through said conductive medium located within said breast duct.

20. An improved method as in claim 19, wherein the energy is applied throughout substantially an entire ductal network.

21. An improved method as in claim 19, wherein the energy is high frequency electrical energy.

22. An improved method as in claim 19, wherein said conductive medium is an electrically conductive medium, and wherein said step of applying energy includes a step of applying electrical energy through said electrically conductive medium.

23. An improved method as in claim 22, wherein applying the electrical energy comprises contacting the electrically conductive medium with an electrode introduced through a ductal orifice.

24. An improved method as in claim 23, further comprising disposing a dispersive electrode on an exterior surface of the breast, wherein a current passes between the electrically conductive medium and the dispersive electrode.

25. An improved method as in claim 24, wherein the energy has a power in the range from 50 W to 300 W.

26. A method for treating a breast duct of a patient, said method comprising:
   introducing into a breast duct targeted for treatment an agent sensitive to at least one selected from the group consisting of light energy, electrical energy, electromagnetic energy, radiation energy and vibrational energy; and
   transferring the specific light, electrical, electromagnetic, radiation or vibrational energy to the agent in the duct in an amount sufficient to disrupt the agent whereupon the agent acts on target cells lining the breast duct.

27. A method as in claim 26, wherein the agent acts ablatively on the target cells lining the breast duct.

28. A method as in claim 26, wherein the agent acts to inhibit proliferation of the target cells lining the breast duct.

29. A method as in claim 26, wherein the agent acts prophylactically on the target cells lining the breast duct.

30. A method as in claim 26, wherein the agent contacts substantially all of the ductal network.

31. A method as in claim 26, wherein the agent contacts a portion of the entire ductal network.

32. A method as in claim 26, further comprising identifying the portion of the ductal network to be treated, wherein energy is transferred only to that portion.

33. A method as in claim 26, wherein transferring energy comprises introducing energy to a lumen of the duct.

34. A method as in claim 26, wherein transferring energy comprises exposing the breast to an energy source.

35. A method as in claim 26, wherein the agent is sensitive to vibrational energy and comprises collagen spheres.

36. A method as in claim 26, wherein the agent is sensitive to light energy comprising wavelengths in the range from ultraviolet to infrared.

37. A method as in claim 35, wherein the agent comprises a photoactive agent selected from the group consisting of porfimer sodium (PHOTOFRIN®), lutetium texaphrin (lutex or Antrin®), temoporfin (Foscan®), and aminolevulinic acid HCl (Levulan®).

38. A method as in claim 26, wherein the agent introduced in the breast duct comprises a resonant frequency of an electromagnetic energy, and electromagnetic energy is transferred to the breast duct.

39. A method as in claim 37, wherein the electromagnetic energy comprises radiofrequency waves or microwaves.

40. A method as in claim 37, wherein the agent comprises a metallic fluid.

41. A method as in claim 39, wherein the metal is gold or silver.

42. A method as in claim 26, wherein the agent is a radiation sensitizer, and the energy comprises x-ray radiation or gamma radiation.

43. A method as in claim 41, wherein the radiation sensitizer comprises gadolinium.

44. A method as in claim 41, wherein the radiation sensitizer comprises texaphyrin.

45. A method for treating a breast duct, said method comprising:
   selecting an individual duct; and
   transferring energy to or from cells lining the duct in an amount sufficient to ablate or inhibit proliferation of said cells, wherein said energy is transferred to or from a device positioned within said duct.

46. A method as in claim 45 further comprising a step of introducing a medium into said duct.

47. A method as in claim 46 wherein the medium is an electrically conductive fluid.

48. A method as in claim 46 further comprising a step of positioning at least a portion of said device in said medium and applying a high frequency current to said medium.

49. A method as in claim 48 wherein said device is an electrically conductive probe.

50. A method for treating a breast duct, said method comprising:
   selecting a breast duct;
   introducing a medium into said breast duct; and
   transferring energy to or from cells lining the duct in an amount sufficient to ablate or inhibit proliferation of said cells.

51. A method as in claim 50 wherein said medium is electrically conductive.

52. A method as is claim 51 wherein said medium is a fluid introduced into the duct through a ductal opening.

53. A method as in claim 51 further comprising a step of introducing a therapeutic device into said duct through a ductal opening and contacting said medium with at least a portion of said therapeutic device.

54. A method as in claim 53 wherein said transferring step includes the step of transferring a high frequency electrical current from said therapeutic device to said medium.

55. A method of treating a breast duct, said method comprising:

selecting a breast duct;

introducing a medium into said breast duct;

introducing a device into said breast duct so that at least a portion of said device contacts said medium; and transferring energy to or from cells lining the duct in an amount sufficient to ablate or inhibit proliferation of said cells.

* * * * *

UNITED STATES PATENT AND TRADEMARK OFFICE
CERTIFICATE OF CORRECTION

PATENT NO. : 6,391,026 B1
APPLICATION NO. : 09/397753
DATED : May 21, 2002
INVENTOR(S) : David Hung et al.

Page 1 of 1

It is certified that error appears in the above-identified patent and that said Letters Patent is hereby corrected as shown below:

In the Specification

Column 1, Line 11 add the Government Support Clause:
--This invention was made with government support under grant number AI033123 awarded by the National Institutes of Health. The government has certain rights in the invention.--

Signed and Sealed this
Eleventh Day of August, 2020

Andrei Iancu
*Director of the United States Patent and Trademark Office*